US011415577B2

(12) United States Patent
Kim et al.

(10) Patent No.: US 11,415,577 B2
(45) Date of Patent: Aug. 16, 2022

(54) METHOD OF DETECTING BIO-MATERIAL

(71) Applicant: ELECTRONICS AND TELECOMMUNICATIONS RESEARCH INSTITUTE, Daejeon (KR)

(72) Inventors: Young Jun Kim, Daejeon (KR); Bongjin Jeong, Sejong (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 356 days.

(21) Appl. No.: 16/669,181

(22) Filed: Oct. 30, 2019

(65) Prior Publication Data

US 2020/0132684 A1    Apr. 30, 2020

(30) Foreign Application Priority Data

Oct. 31, 2018  (KR) .................. KR10-2018-0132591
Oct. 8, 2019   (KR) .................. KR10-2019-0124817

(51) Int. Cl.
   *C12Q 1/6886*   (2018.01)
   *G01N 33/543*   (2006.01)
   *G01N 27/327*   (2006.01)

(52) U.S. Cl.
   CPC ..... *G01N 33/54346* (2013.01); *C12Q 1/6886* (2013.01); *G01N 27/3276* (2013.01); *G01N 27/3278* (2013.01); *C12Q 2600/158* (2013.01); *C12Q 2600/178* (2013.01)

(58) Field of Classification Search
   None
   See application file for complete search history.

(56) References Cited

U.S. PATENT DOCUMENTS

| 8,318,093 | B2 | 11/2012 | Wang et al. |
| 8,529,750 | B2 | 9/2013 | Ah et al. |
| 2010/0273266 | A1 | 10/2010 | Hong et al. |

FOREIGN PATENT DOCUMENTS

| KR | 101763515 B1 | 8/2017 |
| KR | 101888769 B1 | 8/2018 |

OTHER PUBLICATIONS

Wang et al. (Anal Chem Aug. 7, 2012;84(15):6400-6406).*
Lawrie et al., "MicroRNA expression distinguishes between germinal center B cell-like and activated B cell-like subtypes of diffuse large B cell lymphoma," Int. J. Cancer, 2007, pp. 1156-1161, vol. 121.
Calin, et al., "Human microRNA genes are frequently located at fragile sites and genomic regions involved in cancers," PNAS, Mar. 2, 2004, pp. 2993-3004, vol. 101, No. 9.
Cao et al., "Noncoding RNAs in the Mammalian Central Nervous System," Annu. Rev. Neurosci, 2006, pp. 77-103, vol. 29.
Orio et al., "MicroRNA Signatures in Human Ovarian Cancer," Cancer Research, Sep. 15, 2007, pp. 8699-8707, vol. 67, American Association for Cancer.
Qi et al., "Circulating microRNAs (cmiRNAs) as novel potential biomarkers for hepatocellular carcinoma," Neoplasma, Dec. 20, 2013, pp. 135-142, vol. 60.
Porkka et al., "MicroRNA Expression Profiling in Prostate Cancer," Cancer Research, Jul. 1, 2007, pp. 6130-6135, vol. 67.
Wang et al., "Tumor-Associated Circulating MicroRNAs as Biomarkers of Cancer," Molecules, Feb. 10, 2014, pp. 1912-1938, vol. 19.
Duffy et al., "Use of molecular markers for predicting therapy response in cancer patients," Cancer Treatment Reviews, 2011, pp. 151-159, vol. 37, Elsevier Ltd.
Tian et al., "High-Throughput Functional MicroRNAs Profiling by Recombinant AAV-Based MicroRNA Sensor Arrays," PLoS ONE, Jan. 5, 2012, pp. 1-10, vol. 7, Issue 1, e29551.
Koshiol et al., "Strengths and Limitations of Laboratory Procedures for MicroRNA Detection," Cancer Epidemiology, Biomarkers & Prevention, Mar. 23, 2010, pp. 907-911, vol. 19, American Association for Cancer Research.
Yang et al., "Quantification of microRNA by gold nanoparticle probes," Analytical Biochemistry, Feb. 8, 2008, pp. 183-188, vol. 376, Elsevier Inc.
Cui, et al., "Graphene oxide-protected DNA probes for multiplex microRNA analysis in complex biological samples based on a cyclic enzymatic amplification method," Chemical Communications, Jan. 7, 2012, pp. 194-196, vol. 18, No. 2.
Wang et al., "Direct Quantification of MicroRNA at Low Picomolar Level in Sera of Glioma Patients Using a Competitive Hybridization Followed by Amplified Voltammetric Detection," Analytical Chemistry, Jun. 26, 2012, pp. 6400-6406, vol. 84, ACS Publications.
Azimzadeh et al., "An electrochemical nanobiosensor for plasma miRNA-155, based on graphene oxide and gold nanorod, for early detection of breast cancer," Biosensors and Bioelectronics, 2016, pp. 99-106, vol. 77.

(Continued)

*Primary Examiner* — Amanda Haney

(57) ABSTRACT

A method of detecting bio-material includes preparing an electrode where capture structures are fixed on surface of the electrode; preparing nanoparticles where probes are fixed on surfaces of the nanoparticles; providing bio-materials on the nanoparticles so that the probes of a portion of the nanoparticles make complementary bonds with the bio-materials, respectively, to form composites, and another portion of the nanoparticles remain without making bonds with the bio-materials; and providing another portion of the remaining nanoparticles on the surface of the electrode so that the capture structures make complementary bonds with the probes of another portion of the nanoparticles, respectively, wherein each of the capture structures includes nucleotides having first sequence, each of the probes includes nucleotides having second sequence, each of the bio-materials includes nucleotides having third sequence, the first and second sequences are complementary to each other, and the second and third sequences are complementary to each other.

10 Claims, 7 Drawing Sheets

(56) References Cited

OTHER PUBLICATIONS

Wang et al., "Integrated amplified aptasensor with in-situ precise preparation of copper nanoclusters for ultrasensitive electrochemical detection of microRNA 21," Biosensors and Bioelectronics, Jul. 5, 2017, pp. 386-391, vol. 98, Elsevier B.V.

Dong et al., "Highly Sensitive Multiple microRNA Detection Based on Fluorescence Quenching of Graphe," Analytical Chemistry, Apr. 17, 2012, pp. 4587-4593, vol. 84, ACS Publications.

Ryoo et al., "Quantitative and Multiplexed MicroRNA Sensing in Living Cells Based on Peptide Nucleic Acid and Nano Graphene Oxide (PANGO)," ACS NANO, 2013, pp. 5882-5891, vol. 7, No. 7.

Tu et al., "Fluorescence Quenching of Graphene Oxide Integrating with the Site-Specific Cleavage of the Endonuclease for Sensitive and Selective MicroRNA Detection," Analytical Chemistry, Jan. 15, 2013, pp. 2536-2542, vol. 85, ACS Publications.

Kia et al., "Hairpin DNA probe with 5'-TCC/CCC-3' overhangs for the creation of silver nanoclusters and miRNA assay," Biosensors and Bioelectronics, Jul. 26, 2013, pp. 36-39, vol. 51, Elsevier B.V.

Diamandis, "The failure of protein cancer biomarkers to reach the clinic: why, and what can be done to address the problem?," BMC Medicine, 2012, pp. 1-5,10:87.

\* cited by examiner

METHOD OF DETECTING BIO-MATERIAL

CROSS-REFERENCE TO RELATED APPLICATIONS

This U.S. non-provisional patent application claims priority under 35 U.S.C. § 119 of Korean Patent Application No. 10-2018-0132591, filed on Oct. 31, 2018, and Korean Patent Application No. 10-2019-0124817, filed on Oct. 8, 2019, the entire contents of which are hereby incorporated by reference.

BACKGROUND

The present disclosure herein relates to a method of detecting a bio-material, and more particularly, to a method of detecting a bio-material using nanoparticles.

Bio-technology (BT) is a kind of next-generation conversion technologies, and its significance is steadily increasing. Recently, researches on the analysis of a bio-material are increasing. The bio-material may be provided in small quantity. The bio-material may have a small molecular weight. For example, a bio-material relating to hormones may have a small molecular weight. Accordingly, the requirement on analyzing a bio-material having a small molecular weight is increasing. Also, requirement on rapid and accurate methods for analyzing a bio-material is increasing.

SUMMARY

The present disclosure provides a method of detecting an extremely small amount of a bio-material.

The present disclosure also provides a method of detecting a bio-material, with improved sensitivity and accuracy.

The tasks for solving in the inventive concept is not limited to the above-described tasks, and unmentioned other tasks will be clearly understood by a person skilled in the art from the description below.

The present disclosure relates to a method of detecting a bio-material. According to exemplary embodiments of the inventive concept, a method of detecting a bio-material includes preparing an electrode where capture structures are fixed on a surface of the electrode; preparing nanoparticles where probes are fixed on surfaces of the nanoparticles; providing bio-materials on the nanoparticles so that the probes of a portion of the nanoparticles make complementary bonds with the bio-materials, respectively, to form composites, and another portion of the nanoparticles remain without making bonds with the bio-materials; and providing the another portion of the remaining nanoparticles on the surface of the electrode so that the capture structures make complementary bonds with the probes of the another portion of the nanoparticles, respectively, wherein each of the capture structures includes nucleotides having a first sequence, each of the probes includes nucleotides having a second sequence, each of the bio-materials includes nucleotides having a third sequence, the first sequence and the second sequence are in complementary relations to each other, and the second sequence and the third sequence are in complementary relations to each other.

In exemplary embodiments, each of the capture structures may include a chain part and a linker, and the chain part may be one selected from the group consisting of DNA, RNA, and oligonucleotides.

In exemplary embodiments, the first sequence and the third sequence may include the same base sequence.

In exemplary embodiments, the chain part of each of the capture structures may be fixed on the surface of the electrode via the linker.

In exemplary embodiments, the probes on the surfaces of the nanoparticles may be fixed on the surfaces of the nanoparticles through amide bonds.

In exemplary embodiments, the probes may include from 15 to 50 nucleotides.

In exemplary embodiments, the nanoparticles may include silica, gold (Au), or a polymer material.

In exemplary embodiments, the bio-materials may be bio-markers for diagnosing breast cancer, prostate cancer, mental diseases, metabolic diseases, or cardiovascular diseases.

In exemplary embodiments, the bio-materials may include from 15 to 50 nucleotides.

In exemplary embodiments, the bio-materials may include micro RNA (mi RNA).

In exemplary embodiments, the method may further include measuring a current value of the electrode, wherein the measuring of the current value of the electrode may be performed after performing the complementary bonding of the capture structures with the probes of the another portion of the nanoparticles, respectively.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
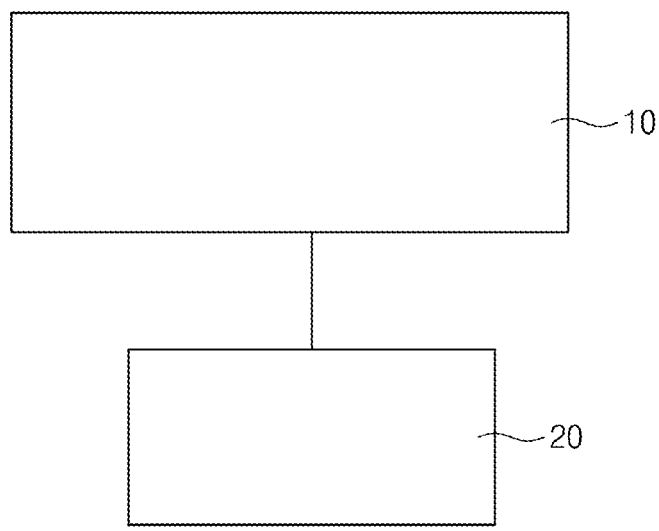
FIG. 1 is a diagram schematically showing an analysis apparatus according to an embodiment.

Hereinafter, preferred embodiments of the inventive concept will be described below in detail with reference to the accompanying drawings. The advantages and the features of the inventive concept, and methods for attaining them will be described in example embodiments below with reference to the accompanying drawings. The inventive concept may, however, be embodied in different forms and should not be construed as limited to the embodiments set forth herein. Rather, these embodiments are provided so that this description will be thorough and complete, and will fully convey the scope of the present inventive concept to those skilled in the art. The inventive concept is defined only by the scope of the claims.

The terminology used herein is for the purpose of describing exemplary embodiments only and is not intended to limit the present inventive concept. As used herein, the singular forms are intended to include the plural forms as well, unless the context clearly indicates otherwise. It will be further understood that the terms "comprises" and/or "comprising," when used in this specification, specify the presence of stated features, steps, operations, and/or devices, but do not preclude the presence or addition of one or more other features, steps, operations, and/or devices thereof. In addition, reference symbols suggested according to the order of explanation should not be limited to their order, because the reference symbols are suggested in preferred embodiments. It will also be understood that when a layer is referred to as being 'on' another layer or substrate, it can be directly on the other layer or substrate, or third intervening layers may also be present.

It will be understood that, although the terms first, second, third etc. may be used herein to describe constituent elements (or structures), regions and layers should not be limited by these terms. These terms are only used to distinguish one constituent element (or structures) from another constituent elements (or structures). Thus, a first structure referred to in an embodiment could be termed a second structure in another embodiment. Example embodiments embodied and described herein may include complementary example embodiments thereof. Like reference numerals refer to like elements throughout.

In the disclosure,

means a connected part.

In the disclosure, a substituted or unsubstituted alkyl group may mean an alkyl group which is substituted or unsubstituted with one or more substituents selected from the group consisting of a hydrogen atom, a deuterium atom, and an alkyl group. In addition, the substituent may be a substituted or unsubstituted substituent. In the disclosure, the substituent may be interpreted as one or more substituents selected from a monovalent substituent or a divalent substituent.

The method of detecting a bio-material according to the inventive concept will be explained.

Figure 2:
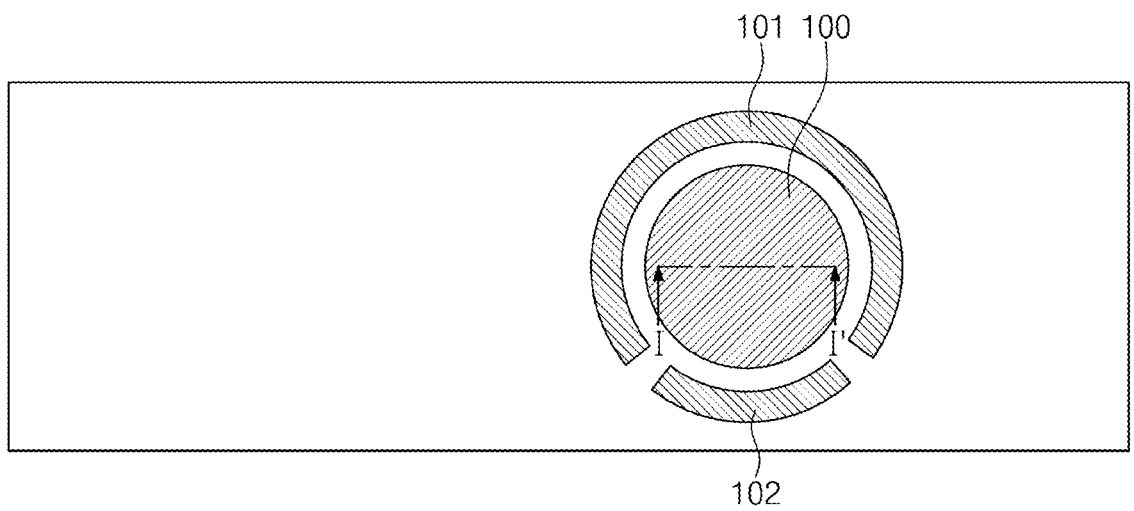
FIG. 2 is a diagram showing electrodes of an analysis apparatus according to an embodiment.

FIG. 1 is a diagram schematically showing an analysis apparatus according to an embodiment. FIG. 2 is a diagram showing electrodes of an analysis apparatus according to an embodiment.

Referring to FIG. 1 and FIG. 2, an analysis apparatus 1 may include a detecting part 10 and a sensing part 20. The analysis apparatus 1 may be used for analyzing a bio-material (not shown). The bio-material (not shown) may be a material to be detected. For example, the bio-material (not shown) may be a bio-marker for diagnosing breast cancer, prostate cancer, mental diseases, metabolic diseases, or cardiovascular diseases. To the detecting part 10, the bio-material (not shown) may be provided. Accordingly, an electrical signal may be generated in the detecting part 10. The electrical signal may be transmitted to the sensing part 20. Though not shown, the analysis apparatus 1 may further include a controlling part and a displaying part. The detecting part 10 may include a plurality of electrodes. For example, the detecting part 10 may include, as shown in FIG. 2, a working electrode 100, a counter electrode 101, and a reference electrode 102.

Figure 3:
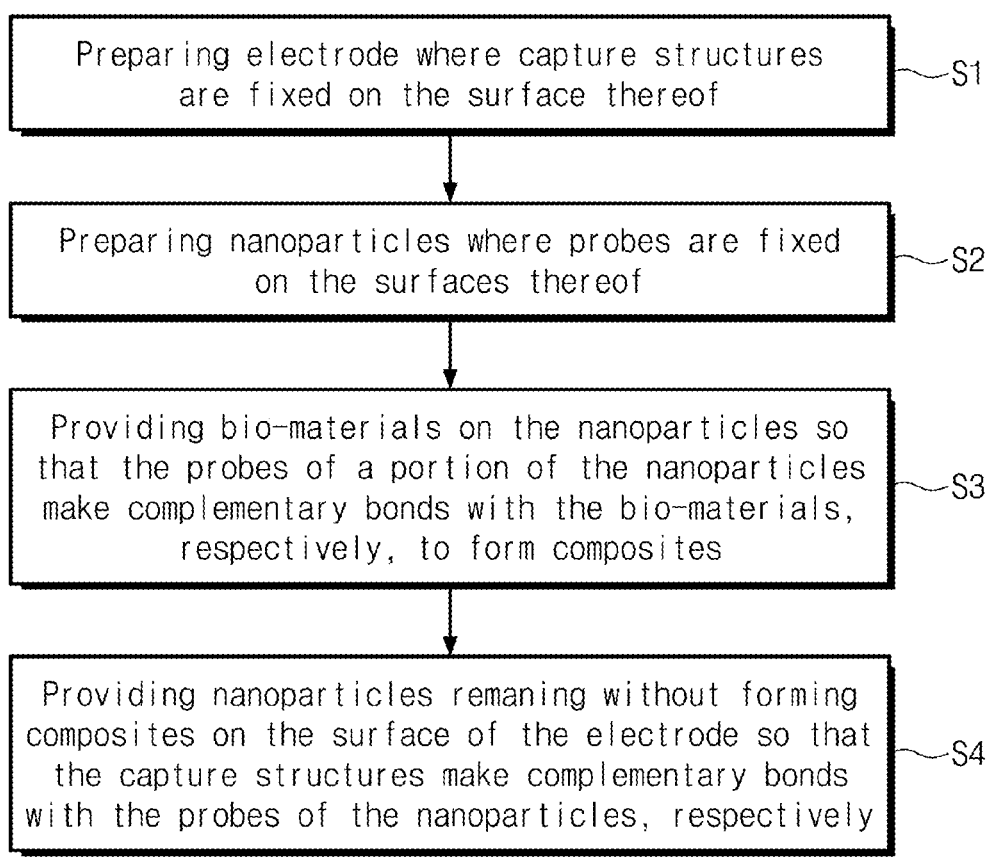
FIG. 3 is a flowchart for explaining a method of detecting a bio-material according to an embodiment.
Figure 4:
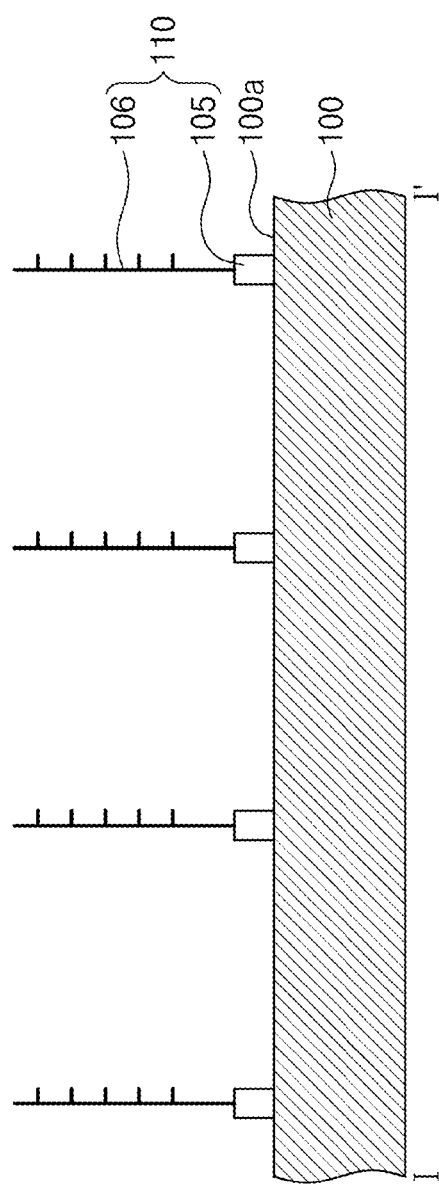
FIG. 4 is a cross-sectional view cut along line I-I' in FIG. 2.

FIG. 3 is a flowchart for explaining a method of detecting a bio-material according to an embodiment. FIG. 4 is a cross-sectional view cut along line I-I' in FIG. 2.

Referring to FIG. 3 and FIG. 4, the method of detecting a bio-material according to an embodiment may include a step of preparing an electrode where capture structures are fixed on a surface of the electrode (S1), a step of preparing nanoparticles where probes are fixed on surfaces of the nanoparticles (S2), a step of providing bio-materials on the nanoparticles so that the probes of a portion of the nanoparticles make complementary bonds with the bio-materials, respectively, to form composites (S3), and a step of providing another portion of the nanoparticles remaining without making bonds with the biomaterials on the surface of the electrode so that the capture structures make complementary bonds with the probes of another portion of the nanoparticles, respectively (S4).

In the step of preparing an electrode where capture structures are fixed on the surface thereof (S1), a working electrode 100 may be prepared. The working electrode 100 may include a conductive material. More particularly, the working electrode 100 may include a carbon-containing material or a metal. The metal may include, for example, gold (Au), and the carbon-containing material may include glass carbon, graphene, and/or screen-printed carbon.

The capture structure 110 may be provided on the surface 100a of the working electrode 100. The capture structure 110 may include a linker 105 and a chain part 106. The chain part 106 of the capture structure 110 may include one selected from the group consisting of DNA, RNA, and oligonucleotides. Preferably, the chain part 106 of the capture structure 110 may include from 15 to 50 nucleotides. The chain part 106 of the capture structure 110 may include the same base sequence as that of the bio-material (not shown).

The capture structure 110 may be fixed on the surface 100a of the working electrode 100 via the linker 105. Hereinafter, referring to FIG. 4 and <Reaction 1>, a fixing method of the capture structure 110 will be explained.

For example, in case where the working electrode 100 includes graphene, a reduced graphene oxide (rGO) may be formed by reducing the graphene. Since the reduced graphene oxide has a hydroxide group (—OH), the hydroxide group (—OH) may be provided on the surface 100a of the working electrode 100. The linker 105 may be formed as in <Reaction 1>. The linker 105 of the capture structure 110 may include a group represented by <Formula 2> below. Accordingly, the chain part 106 of the capture structure 110 may be fixed on the surface 100a of the working electrode 100. The chain part 106 of the capture structure 110 may make a complementary bond with a probe 210 on the surface of a nanoparticle 200.

<Reaction 1>

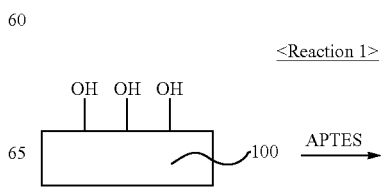

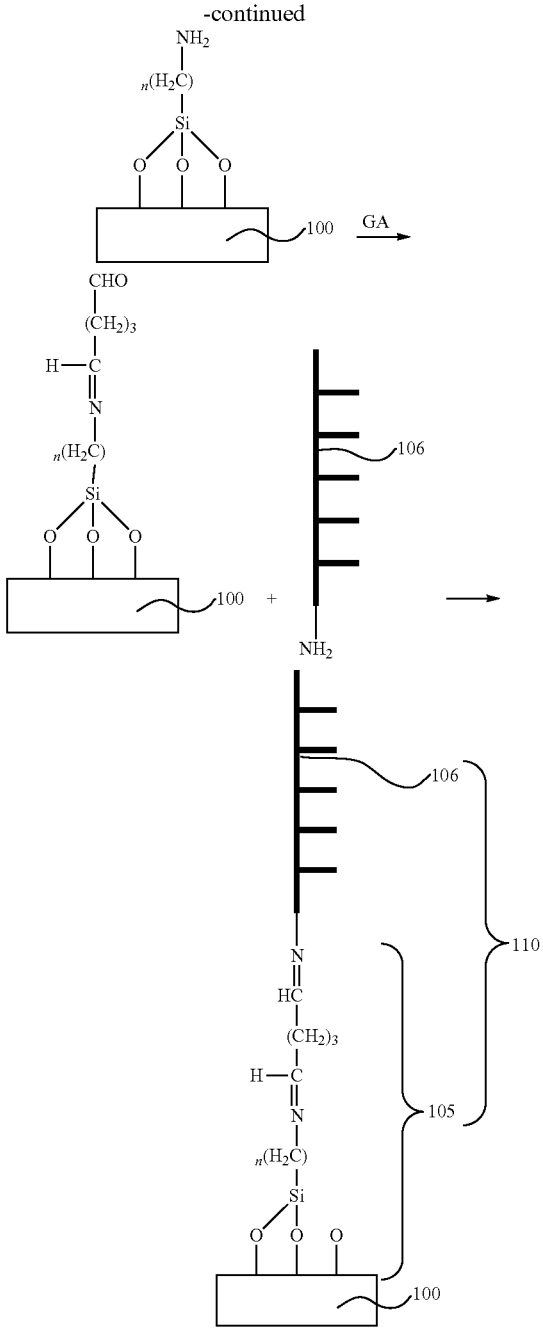

(In <Reaction 1>, APTES may be represented by <Formula 1> below. In <Reaction 1>, GA may be CHO(CH$_2$)$_3$CHO.)

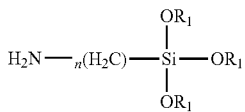

<Formula 1>

(In <Formula 1>, R$_1$ is an alkyl group of 1 to 3 carbon atoms, an n is an integer of 1 to 5. <Formula 1> may include, for example, 3-aminopropyl triethoxysilane.)

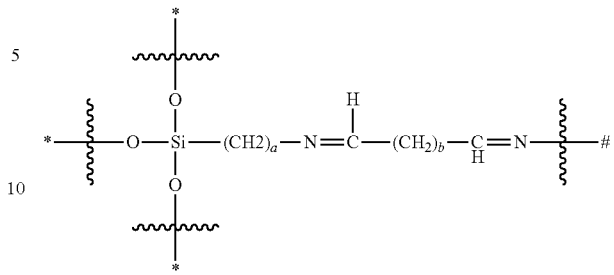

<Formula 2>

(In <Formula 2>, a and b are each independently an integer between 1 and 5. * may mean a bonded part with the working electrode 100. # may mean a bonded part with the chain part 106 of the capture structure 110.)

In another embodiment, in case where the working electrode 100 includes gold (Au), an amine group (—NH$_2$) or a thiol group (—SH) at the terminal of the chain part 106 or the capture structure 110 may be adsorbed on the surface 100a of the working electrode 100. Accordingly, the chain part 106 of the capture structure 110 may be fixed on the working electrode 100. By the method described above, the working electrode 100 where the capture structure 110 is fixed on the surface 100a may be prepared.

Figure 5:
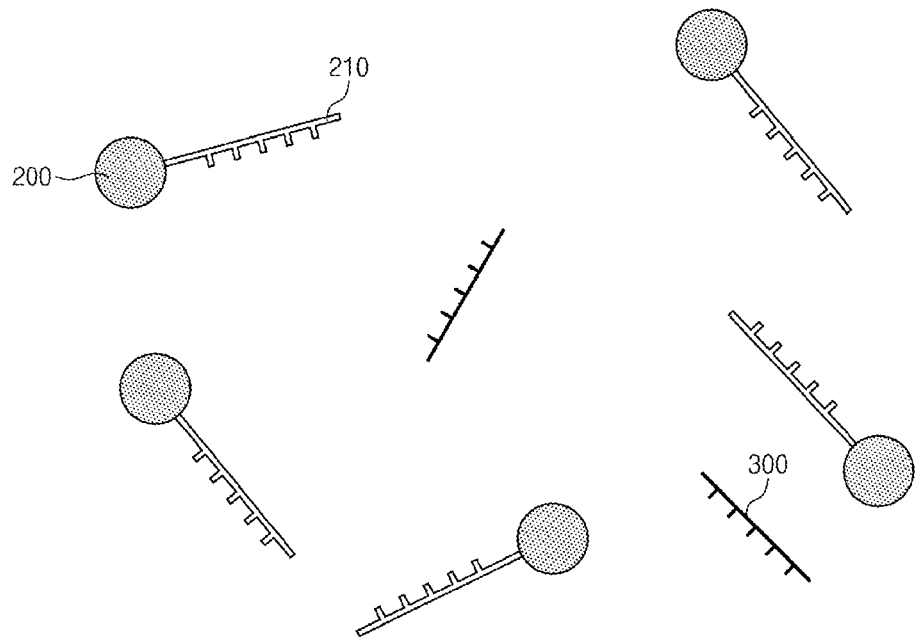
FIG. 5 and FIG. 6 are schematic diagrams for explaining the bonding of nanoparticles and bio-materials.

Referring to FIG. 3 and FIG. 5, in the step of preparing nanoparticles where probes are fixed on the surface thereof (S2), nanoparticles 200 may be prepared. The nanoparticles 200 may include a metal material, a polymer material, or silica. For example, the metal material may include gold (Au), silver (Ag), and/or copper (Cu). In case where the nanoparticles 200 include the metal material, the diameter of the nanoparticle 200 may be from about 2 nm to about 100 nm. In case where the nanoparticles 200 include the silica or the polymer material, the diameter of the nanoparticles 200 may be from about 10 nm to about 200 nm. On the surface of the nanoparticles 200, a hydroxyl group (—OH) or a carboxyl group (—COOH) may be provided. In case where the nanoparticles 200 include the polymer material, for example, the nanoparticles 200 may be synthesized by copolymerizing a styrene monomer and a hydroxyethyl methacrylate (MEMA) monomer. In another embodiment, the nanoparticles 200 may be synthesized by copolymerizing an acrylic monomer and a hydroxyethyl methacrylate (MEMA) monomer.

Probes 210 may be formed on the surfaces of the nanoparticles 200. The probes 210 may include one selected from the group consisting of DNA, RNA, and oligonucleotides, and preferably, the probes 210 may include from 15 to 50 nucleotides. For example, the probes 210 may be micro RNA. In case where the probes 210 include 14 or less nucleotides, the number of the nucleotides for making selective bonds between the probes 210 and bio-materials having a complementary base sequence may be insufficient. Accordingly, the accuracy for detecting the bio-material 300 may be degraded. In case where the probes 210 include 51 or more nucleotides, time required for making bonds between the probes 210 and the bio-materials 300 may be prolonged. Accordingly, the detecting rate of the bio-material 300 may decrease.

Hereinafter, referring to <Reaction 2> and <Reaction 3>, a method of forming probes 210 will be explained. The probes 210 may have a complementary base sequence to the bio-material 300 or the chain part 106 of the capture structure 110. Accordingly, the probes 210 may make complementary bonds with the bio-materials 300 or the chain parts 106 of the capture structures 110. In case where hydroxyl groups (—OH) are provided on the surface of the nanoparticles 200, the probes 210 may be fixed on the surfaces of the nanoparticles 200 as in <Reaction 1>.

In another embodiment, in case where carboxyl groups (—COOH) are provided on the surfaces of the nanoparticles 200, the probes 210 may be fixed on the surfaces of the nanoparticles 200 as in <Reaction 2> or <Reaction 3> below. By the above-described methods, nanoparticles 200 where probes 210 are fixed on the surfaces thereof may be prepared.

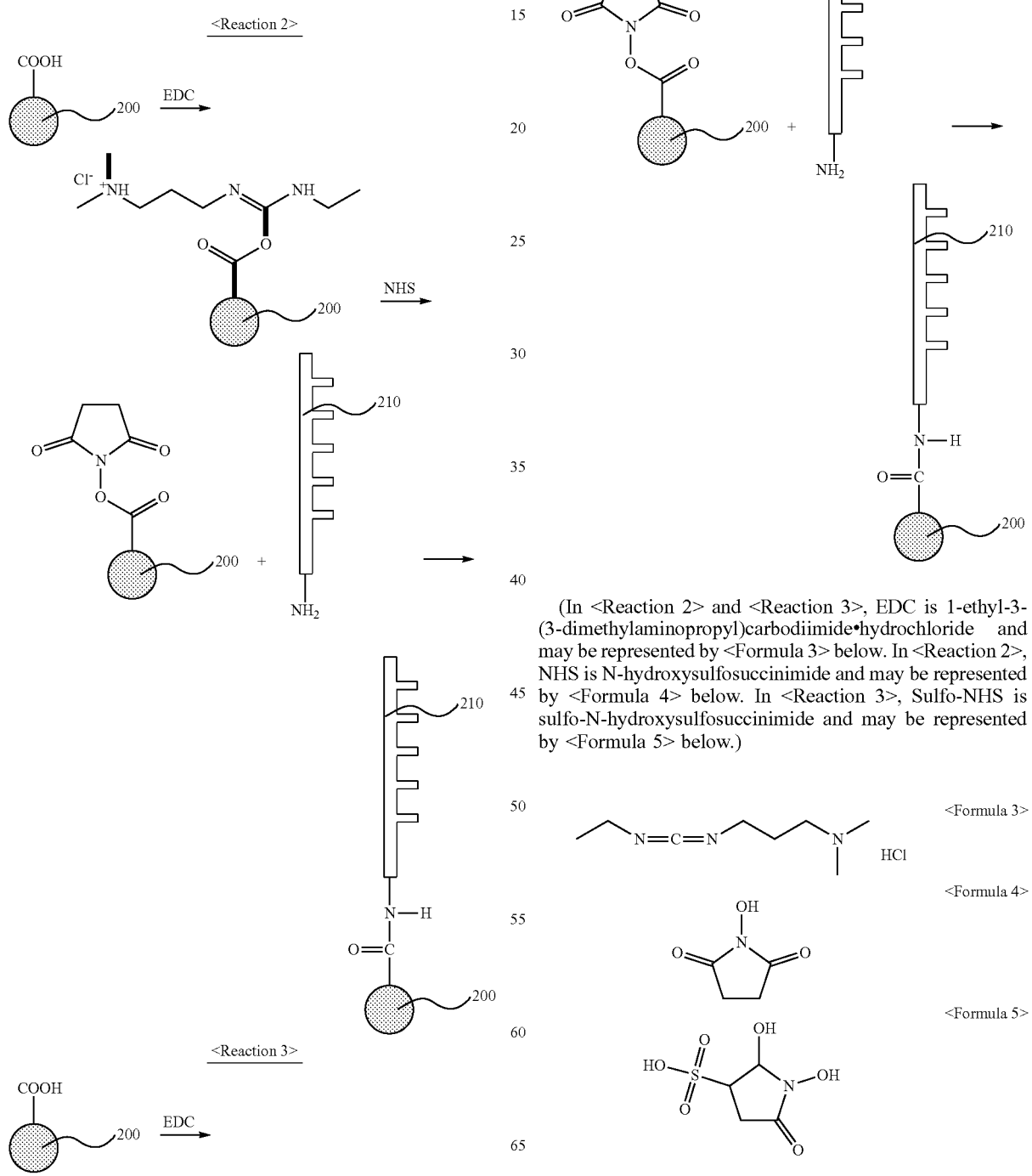

(In <Reaction 2> and <Reaction 3>, EDC is 1-ethyl-3-(3-dimethylaminopropyl)carbodiimide•hydrochloride and may be represented by <Formula 3> below. In <Reaction 2>, NHS is N-hydroxysulfosuccinimide and may be represented by <Formula 4> below. In <Reaction 3>, Sulfo-NHS is sulfo-N-hydroxysulfosuccinimide and may be represented by <Formula 5> below.)

Figure 6:
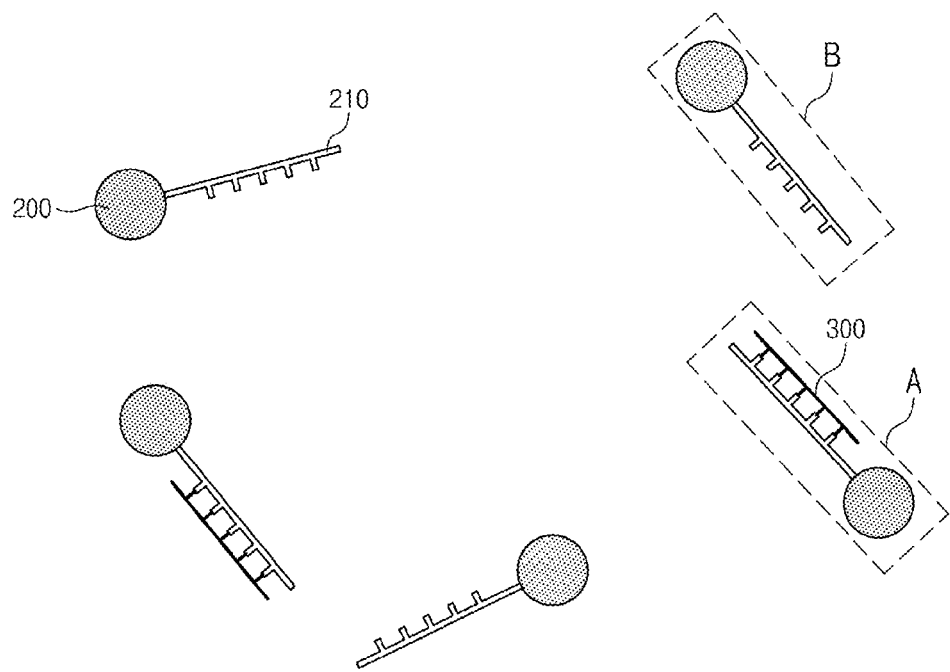

FIG. 5 and FIG. 6 are schematic diagrams for explaining the bonding of nanoparticles and bio-materials.

Referring to FIG. 5 and FIG. 6, in the step of forming composites by providing bio-materials on the nanoparticles to make complementary bonds between the probes of a portion of the nanoparticles and the bio-materials, respectively (S3), the bio-materials 300 may be provided on the nanoparticles 200. More particularly, the nanoparticles 200 and the bio-materials 300 may be provided in a solvent (not shown). The solvent may further include an ionic compound (not shown). The ionic compound may cause an electric current to flow through the solvent. The bio-materials 300 may be obtained from the blood, urine, saliva, etc. of people or animals. The bio-materials 300 are present in small quantity in a living body and may be obtained in small quantity. Accordingly, the number of the nanoparticles 200 in the solvent may be greater than the number of the bio-materials 300. The bio-materials 300 include one selected from the group consisting of DNA, RNA, and oligonucleotides, and may preferably include from 15 to 50 nucleotides. For example, the bio-materials 300 may be micro RNA (miRNA). In case where the bio-materials 300 include 14 or less nucleotides, the number of the nucleotides for making selective bonds between the bio-materials 300 and the probes 210 having a complementary base sequence may be insufficient. Accordingly, the detection accuracy of the bio-materials 300 may be degraded. In case where the bio-materials 300 include 51 or more nucleotides, time required for making bonds between the bio-materials 300 and probes 210 may be prolonged. Accordingly, the detection rate of the bio-materials 300 may decrease. The bio-materials 300 may include a complementary base sequence to the probe 210. Accordingly, the probes of a portion of the nanoparticles 200 may make complementary bonds with the bio-materials 300, respectively, to form composites (A of FIG. 6). Another portion of the nanoparticles 200 may remain without forming a composite (B of FIG. 6).

Figure 7:
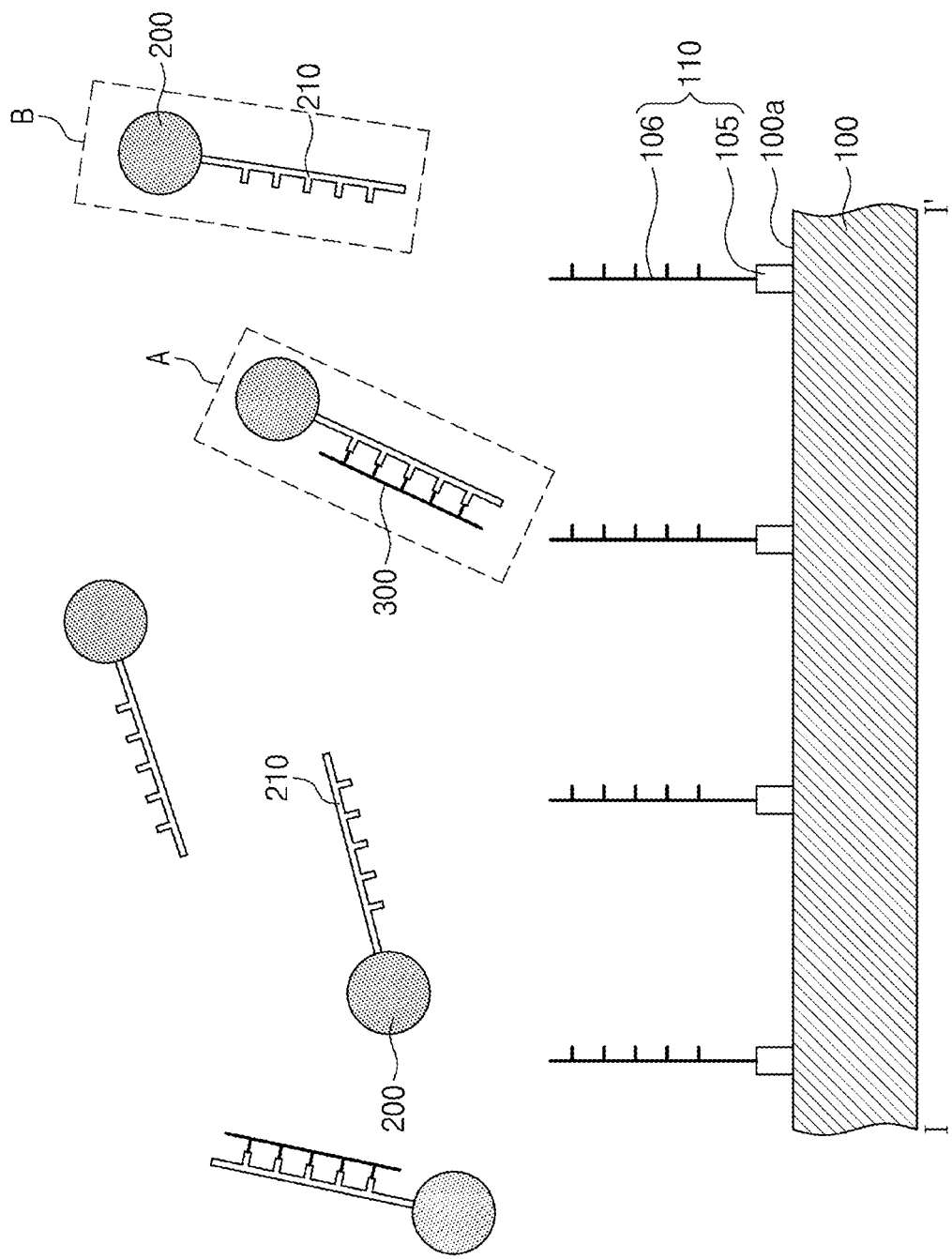
FIG. 7 is a schematic diagram showing a provided state of nanoparticles and composites on a working electrode.
Figure 8:
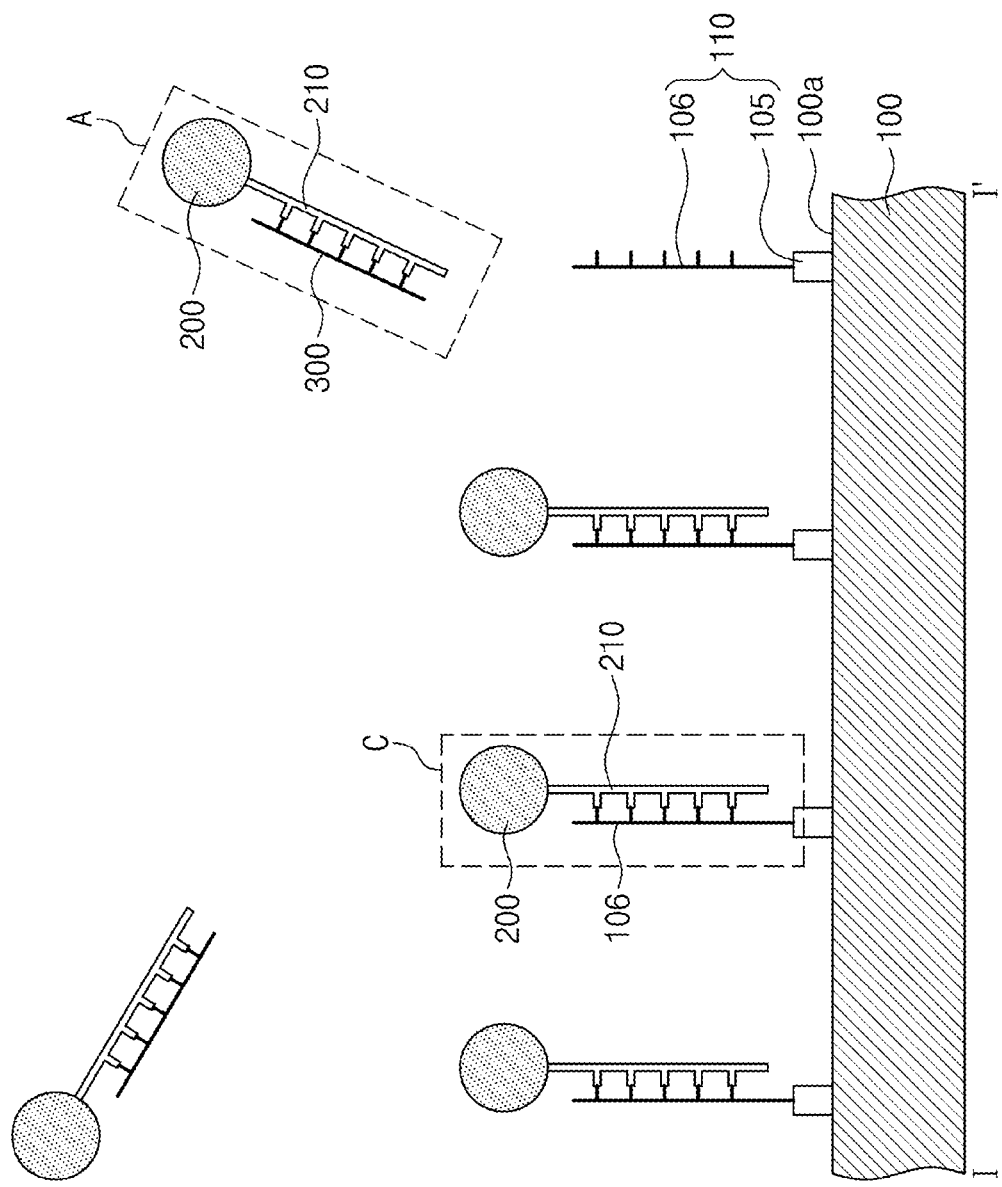
FIG. 8 is a schematic diagram showing a bonded state of probes fixed on the surface of nanoparticles with capture structures or bio-materials.

FIG. 7 is a schematic diagram showing a provided state of nanoparticles and composites on a working electrode. FIG. 8 is a schematic diagram showing a bonded state of probes fixed on the surfaces of nanoparticles with capture structures or bio-materials.

Referring to FIG. 7 and FIG. 8, in the step of providing the remaining nanoparticles which do not form a composite on the surface of the electrode to make complementary bonds between the capture structures and the probes of the nanoparticles (S4), the composites (A of FIG. 7) and the remaining nanoparticles 200 which do not form a composite (B of FIG. 7) may be provided on the surface 100a of a working electrode 100. After that, the working electrode 100 may be left for a certain time period. The certain time period may be, for example, from about 20 minutes to about 40 minutes. Accordingly, a time period required for making bonds between the probes 210 of the nanoparticles 200 and a plurality of chain parts 106 on the surface 100a of the working electrode 100 may be provided. More particularly, the probes 210 of the remaining nanoparticles 200 which do not form the composite B may make complementary bonds with the chain parts 106 after the certain time period (C of FIG. 8). In case where the nanoparticles 200 include an insulating material, for example, silica or a polymer material, the intensity of current measured at the working electrode 100 may decrease in accordance with the fixing of the nanoparticles 200 on the surface 100a of the working electrode 100. In another embodiment, in case where the nanoparticles 200 include a metal material, the intensity of current measured at the working electrode 100 may decrease in accordance with the fixing of the nanoparticles 200 on the surface 100a of the working electrode 100.

According to the inventive concept, the probes 210 on the surface of the nanoparticles 200 may make complementary bonds with the bio-materials 300. The probes 210 of a portion of the nanoparticles 200 may be bonded to the bio-materials 300 to form composites A. Another portion of the nanoparticles 200 which do not form a composite B may be provided on the working electrode 100. Accordingly, the probes 210 of another portion of the nanoparticles 200 may make complementary bonds with the chain parts 106 of the capture structures 110, respectively. Since the capture structures 110 are bonded to the nanoparticles 200 which do not form a composite B, the number of the nanoparticles 200 fixed on the working electrode 100 may be changed in accordance with the number of the bio-materials 300. Since the nanoparticles 200 are fixed on the working electrode 100, the intensity of current measured at the working electrode 100 may be changed, and by measuring and analyzing the intensity of current measured at the working electrode 100, the bio-materials 300 may be detected. The method of detecting a bio-material according to the inventive concept may not need a step of amplifying bio-materials 300 using the nanoparticles 200 (polymerase chain reaction; PCR). Accordingly, a more rapid method of detecting a bio-material, with improved sensitivity may be provided.

Hereinafter, the evaluation results on the intensity of current measured at a working electrode according to the experimental examples of the inventive concept will be explained.

EXPERIMENTAL EXAMPLES

In order to form a capture structure on the surface of a working electrode, first micro RNA which functions as a bio-marker for diagnosing breast cancer is prepared. As in the methods explained referring to <Reaction 1> and <Reaction 2>, the first micro RNA is fixed on the surface of the working electrode to form a capture structure. A nanoparticle including silica is prepared. The diameter of the nanoparticle is from about 2 nm to about 100 nm. In order to form a probe on the surface of the nanoparticle, second micro RNA having a complementary base sequence to the first micro RNA is prepared. As in the method explained referring to <Reaction 2>, the second micro RNA is fixed on the surface of the nanoparticle to form a probe. In order to prepare a sample to be analyzed, various buffer solutions are prepared as solvents. In the solvent, a plurality of the nanoparticles and a plurality of the first micro RNAs as bio-materials are dispersed to prepare samples to be analyzed. Nine samples to be analyzed are prepared by changing the molar concentration of the first micro RNA. More particularly, the molar concentrations of the first micro RNA of the nine samples to be analyzed are 10 aM, 100 aM, 1 fM, 10 fM, 100 fM, 1 pM, 10 pM, 100 pM, and 1 nM. The concentration of the nanoparticles of the samples to be analyzed is about 0.74 uM. 10 uL of each of the samples to be analyzed is loaded on the surface of the working electrode. After loading the sample to be analyzed, a reaction time period of about 30 minutes is provided in temperature conditions of about 37° C. After the reaction time, a current value flowing through the working electrode is measured.

Figure 9:
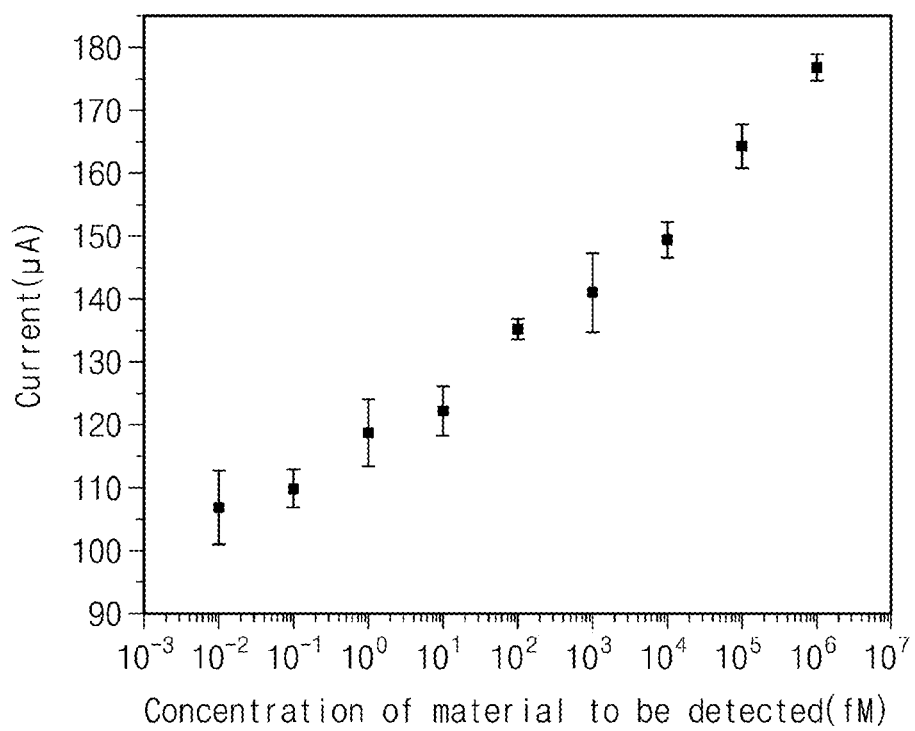
FIG. 9 is a graph showing correlation between a current intensity measured by an analysis apparatus according to an embodiment and a concentration of bio-materials.

FIG. 9 is a graph showing correlation between a current intensity measured by an analysis apparatus according to an embodiment and a concentration of bio-materials. Referring to FIG. 9, it could be confirmed that the intensity of current measured increases in accordance with the increase of the concentration of the bio-materials.

According to the method of detecting a bio-material according to exemplary embodiments of the inventive concept, the detection time of the bio-material to be detected may be reduced.

According to the method of detecting a bio-material according to exemplary embodiments of the inventive concept, the detection sensitivity of the bio-material to be detected may be improved.

The effects of the inventive concept are not limited to the above-described effects, and unmentioned other effects will be clearly understood by a person skilled in the art from the description above.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method of measuring a concentration of bio-materials in a sample, the method comprising:
    preparing a plurality of electrodes having capture structures;
    preparing nanoparticles having probes;
    providing the bio-materials and the nanoparticles in a solvent to form first composites in which the bio-materials and a portion of the probes are bound;
    providing the solvent on the electrodes to form second composites in which the capture structures and another portion of the probes are bound;
    measuring a current value between the electrodes using the second composites; and
    comparing the current value with a reference current to obtain the concentration of the bio-materials bound to the probes,
    wherein each of the capture structures comprises nucleotides having a first sequence,
    each of the probes comprises nucleotides having a second sequence,
    each of the bio-materials comprises nucleotides having a third sequence,
    the first sequence and the second sequence are complementary, and
    the second sequence and the third sequence are complementary.

2. The method of claim 1, wherein each of the capture structures comprises a chain part and a linker, and
    the chain part is one selected from the group consisting of DNA, RNA, and oligonucleotides.

3. The method of claim 2, wherein the first sequence and the third sequence comprise the same base sequence.

4. The method of claim 2, wherein the chain part of each of the capture structures is fixed on the surface of the electrode via the linker.

5. The method of claim 1, wherein the probes of the surfaces of the nanoparticles are fixed on the surfaces of the nanoparticles through amide bonds.

6. The method of claim 1, wherein the probes are from 15 to 50 nucleotides long.

7. The method of claim 1, wherein the nanoparticles comprise silica, gold (Au), or a polymer material.

8. The method of claim 1, wherein the bio-materials are bio-markers for diagnosing breast cancer, prostate cancer, mental diseases, metabolic diseases, or cardiovascular diseases.

9. The method of claim 1, wherein the bio-materials are from 15 to 50 nucleotides long.

10. The method of claim 1, wherein the bio-materials comprise micro RNA (mi RNA).

* * * * *